(12) United States Patent
Kirkin et al.

(10) Patent No.: US 9,771,558 B2
(45) Date of Patent: Sep. 26, 2017

(54) METHOD FOR GENERATING DENDRITIC CELLS EMPLOYING DECREASED TEMPERATURE

(75) Inventors: Alexei Kirkin, Copenhagen (DK); Karine Djandjougazian, Copenhagen (DK); Jesper Zeuthen, Hellerup (DK)

(73) Assignee: DANDRIT DIOTECH A/S, Copenhagen O (DK)

( * ) Notice: Subject to any disclaimer, the term of this patent is extended or adjusted under 35 U.S.C. 154(b) by 1300 days.

(21) Appl. No.: 12/086,050

(22) PCT Filed: Dec. 7, 2006

(86) PCT No.: PCT/DK2006/000694
§ 371 (c)(1),
(2), (4) Date: Jun. 5, 2008

(87) PCT Pub. No.: WO2007/065439
PCT Pub. Date: Jun. 14, 2007

(65) Prior Publication Data
US 2009/0196856 A1    Aug. 6, 2009

(30) Foreign Application Priority Data
Dec. 8, 2005  (DK) ................................. 2005 01742

(51) Int. Cl.
| | |
|---|---|
| A61K 35/12 | (2015.01) |
| C12N 5/00 | (2006.01) |
| C12N 5/0784 | (2010.01) |
| A61K 39/00 | (2006.01) |

(52) U.S. Cl.
CPC .... C12N 5/0639 (2013.01); A61K 2039/5154 (2013.01); C12N 2501/22 (2013.01); C12N 2501/23 (2013.01); C12N 2501/25 (2013.01); C12N 2523/00 (2013.01)

(58) Field of Classification Search
None
See application file for complete search history.

(56) References Cited

U.S. PATENT DOCUMENTS

| | | | | |
|---|---|---|---|---|
| 5,849,589 | A * | 12/1998 | Tedder et al. ................. | 435/377 |
| 5,976,833 | A * | 11/1999 | Furukawa et al. ............ | 435/69.1 |
| 2002/0182194 | A1 | 12/2002 | Ju et al. | |
| 2004/0009596 | A1 | 1/2004 | Rao et al. | |
| 2005/0003533 | A1 | 1/2005 | Kalinski | |
| 2005/0084966 | A1* | 4/2005 | Edelson ............. | A61K 39/0011 435/372 |
| 2005/0123522 | A1* | 6/2005 | Punnonen et al. ......... | 424/93.21 |
| 2009/0053251 | A1* | 2/2009 | Pogue-Caley et al. .... | 424/184.1 |

FOREIGN PATENT DOCUMENTS

| | | | |
|---|---|---|---|
| JP | 2004-166697 A | 6/2004 | |
| WO | 2004/092220 A1 | 10/2004 | |
| WO | 2006127150 A2 | 11/2006 | |
| WO | WO 2006/127150 | * 11/2006 | ............... C12N 5/06 |

OTHER PUBLICATIONS

Farbman et al., "Growth of Olfactory Epithelial Tissue in Vitro: Lectin Staining of Axons", Microscopy Research and Technique, 1992, vol. 23, pp. 173-180.*
Larsson et al., "Lack of phenotypic and functional impairment in dendritic cells from chimpanzees chronically infected with hepatitis C virus", Journal of Virology, Jun. 2004, vol. 78, No. 12, pp. 6151-6161.*
Heufler, C., et al., "Interleukin-12 is produced by dendritic cells and mediates T helper 1 development as well as interferon-γ production by T helper 1 cells", Eur. J. Immunol., vol. 26, pp. 659-668, (1996).
Dexter, T.M., et al., "Conditions Controlling the Proliferation of Haemopoietic Stem Cells In Vitro", J. Cell. Physiol., vol. 91, pp. 335-344, (1976).
Chen, M., et al., "Therapeutic effect of autologous dendritic cell vaccine on patients with chronic hepatitis B: A clinical study", World J Gastroenterol, vol. 11, No. 12, pp. 1806-1808, (2005).
Basu, S., et al., "Fever-like temperature induces maturation of dendritic cells through induction of hsp90", International Immunology, vol. 15, No. 9, pp. 1053-1061, (2003).
Athanasas-Platsis, S., et al., "Induction of the CD1a Langerhans Cell Marker on Human Monocytes", Archs oral Biol., vol. 40, No. 2, pp. 157-160, (1995).
Jonuleit, H., et al., "Pro-inflammatory cytokines and prostaglandins induce maturation of potent immunostimulatory dendritic cells under fetal calf serum-free conditions", Eur. J. Immunol., vol. 27, pp. 3135-3142, (1997).
Sallusto, F., et al., "Efficient Presentation of Soluble Antigen by Cultured Human Dendritic Cells is Maintained by Granulocyte/Macrophage Colony-stimulating Factor Plus Interleukin 4 and Downregulated by Tumor Necrosis Factor α", J. Exp. Med., vol. 179, pp. 1109-1118, (1994).
Romani, N., et al., "Proliferating Dendritic Cell Progenitors in Human Blood", J. Exp. Med., vol. 180, pp. 83-93, (1994).
Peters, J.H., et al., "Signals Required for Differentiating Dendritic Cells from Human Monocytes In Vitro", Dendritic in Fundamental and Clinical Immunology, Edited by Kamperdijk, et al., Plenum Press, New York, 1993. p. 275-280.
Lu, W., et al., "Therapeutic dendritic-cell vaccine for chronic HIV-1 infection", Nature Medicine, vol. 10, No. 12, pp. 1359-1365, (2004).

(Continued)

*Primary Examiner* — Laura Schuberg
(74) *Attorney, Agent, or Firm* — Nath, Goldberg & Meyer; Joshua B. Goldberg; Tanya E. Harkins (57) ABSTRACT

The invention relates in certain embodiments to a method for generating dendritic cells by employing temperatures below 37° C. during the development of progenitor cells and immature dendritic cells. In some embodiments the invention relates to populations of dendritic cells and its use.

6 Claims, 10 Drawing Sheets
(9 of 10 Drawing Sheet(s) Filed in Color)

(56) References Cited

OTHER PUBLICATIONS

Lehmann, M.H., "Recombinant human granulocyte-macrophage colony-stimulating factor triggers interleukin-10 expression in the monocytic cell line U937", Molecular Immunology, vol. 35, pp. 479-485, (1998).
Kirkley, J.E., et al., "Temperature Alters Lipopolysaccharide-Induced Cytokine Secretion by Raw 264.7 Cells", Scandinavian Journal of Immunology, vol. 58, pp. 51-58, (2003).
Scandella, E., et al., "Prostaglandin E2 is a key factor for CCR7 surface expression and migration of monocyte-derived dendritic cells", Blood, vol. 100, No. 4, pp. 1354-1361, (2002).
Volkmann, A., et al., "A conditionally immortalized dendritic cell line which differentiates in contact with T cells or T cell-derived cytokines", Eur. J. Immunol., vol. 26, pp. 2565-2572, (1996).
Aiba, S., et al., "In vitro treatment of human transforming growth factor-β1-treated monocyte-derived dendritic cells with haptens can induce the phenotypic and functional changes similar to epidermal Langerhans cells in the initiation phase of allergic contact sensitivity reaction," Immunology, 2000, pp. 68-75, vol. No. 101, No. 1, Blackwell Science Ltd.
Wang, Z-Y, et al., "Effects of gold sodium thiomalate on the differentiation of dendritic cells from peripheral blood monocytes," Japanese Journal of Clinical Immunology, pp. 1-3, vol. 24, No. 5.
Dalboni et al., "Tumour necrosis factor-α plus interleukin-10 low producer phenotype predicts acute kidney injury and death in intensive care unit patients", Clin Exp Immunol. Aug. 2013 ,173(2)242-9.
Schotte et al., "Putative IL-10 Low Producer Genotypes Are Associated with a Favourable Etanercept Response in Patients with Rheumatoid Arthritis", PLoS One, Jun. 201510(6) from eCollection 2015.

* cited by examiner

Fig. 1

A: Effect of temperature on the expression of DC markers

Fig. 2

Effect of temperature on IL-10 production by immature and mature DC

Fig. 3
Expression of IL-12

Fig. 4

Expression of CCR7 by mature DC generated at various temperatures

Fig. 5A
Comparison of phenotype of immature and mature DC generated by the new method

Fig. 5B
Comparison between DC generated according to the new method and DC generated by a standard method.

Day 5 immature DC's
— Standard
····· New

Day 8 Mature DC's
— Standard
····· New Method

Fig. 6
Stability test

Fig. 7

DC maintain the phenotype and the T cell stimulatory capacity until day 10

Fig. 8

The allo-reactivity of dendritic cells generated either by a "standard method" (old) or the method of the invention (new).

Fig. 9

ELISPOT

METHOD FOR GENERATING DENDRITIC CELLS EMPLOYING DECREASED TEMPERATURE

TECHNICAL FIELD

The invention relates to methods and means useful for inducing immune responses against malignancies and infectious diseases. More particularly, the invention pertains to improved methods for generating antigen presenting cells.

BACKGROUND ART

Dendritic cell-based immune therapies that exploit natural mechanisms of antigen presentation represent the most promising non-toxic method of cancer treatment. It may be used as a sole treatment, or as an adjuvant for other types of therapies such as e.g. surgery, irradiation and chemotherapy. The strategy is based on ex vivo manipulation and reintroduction of cellular products to circumvent immune competences for the purpose of inducing tumor specific immune responses. Thus, the ultimate goal of such dendritic cell-based immune therapies is the induction of tumor-specific effector cells in vivo and recent advances has focused on CD8+ cytotoxic T lymphocytes (CTL) capable of recognizing and killing tumor cells. In addition, the treatment of infectious diseases such as e.g. HIV may benefit from dendritic cell-based vaccination strategies.

Antigen Presentation

Induction of tumor specific immune responses require the engagement of professional antigen presenting cells (APC) expressing Major Histocopatibility Complex (MHC) molecules as well as membrane bound and secreted co-stimulatory molecules. Furthermore, such APC must be able to take up, process and present antigens in association with MHC molecules.

Dendritic cells (DC) are the professional APC of the immune system with the ability to activate both naïve and memory T cells. The stages leading to DC maturation are associated with certain properties of the cell. Immature DC are particularly good in taking up extra-cellular antigens by phagocytosis or pinocytosis and processing the antigens to peptides in the endocytotic compartment such as endosomes and phagosomes. Here the peptides are bound to MHC class II molecules. Immature DC do also have the unique ability of loading the peptides from exogenous proteins to the MHC class I pathway of presentation, a process called cross-presentation.

The ability to efficiently stimulate an immune response by activating CD4+ type I helper T-cells (Th1 cells) and CD8+ cytotoxic T cells (CTL) is crucially dependent on a mature DC. Only fully mature DC equipped with a panel of membrane bound co-stimulatory and accessory molecules such as e.g. CD40, CD80, CD83, CD86 and MHC class II may efficiently induce proliferation and differentiation of antigen-specific T lymphocytes[1].

A significant role of the co-stimulatory activity of DC is provided by secreted cytokines in particular IL-12p70. Its role in the activation of T cells and their polarization to a Th1 type response was clearly demonstrated by Heufler et al. (1996)[1]. Furthermore, a good correlation between the presence of IL-12-expressing mature DC in the tumor and the survival of the patient was reported by Inoue et al. (2005). Mature DC for vaccination purpose should produce limited amounts of the Th1 cell inhibitory cytokine IL-10.

CCR7 is the receptor for the chemokines CCL19 and CCL21 which are produced by stroma cells in lymph nodes. DC expressing sufficient levels of activated CCR7 migrate to the lymph node in response to CCL19 or CCL21[2]. Here they meet T lymphocytes and may initiate an immune response.

Protocols for Generation of Mature DC

Many protocols for the generation of mature DC have been described. The currently most often used "standard" protocol for induction of DC employs a maturation cocktail consisting of IL-1beta, IL-6, TNF-alpha and prostaglandin E2. In spite of migratory activity due to CCR7 and immuno stimulatory activity in vivo, DC matured by this cocktail generates DC with reduced ability to produce IL12p70[3]

A second group of DC maturation protocols comprises polyinosinic:polycytidylic acid, poly-(I:C). It is usually used in combination with cytokines such as TNF alpha, IL-1 beta, IFN-gamma and IFN-alpha. DC generated by this method produces IL-12p70, but they usually express low levels of CCR7. Low levels of CCR7 expression characterized for DC obtained in the presence of poly-(I:C) restrict their in vivo migration to lymph nodes.

Recently, a published patent application US2005/0003533A1 disclosed a method for maturation of dendritic cells expressing CCR7 which subsequently upon CD40L stimulation could be induced to produce IL-12p70.

There is therefore still an unmet requirement for development of standardized methods for generating mature dendritic cells expressing high levels of activated CCR7 and which also produce sufficient amount of IL-12p70.

Furthermore, despite the efforts of many investigators, dendritic cell-based vaccines for use in cancer therapy have in general provided immune responses with modest clinical efficacy. These vaccines have mainly been produced by ex vivo manipulation and antigen-loading of autologous DC. Increasing demands with respect to patient safety requires high level of reproducibility and compliance with regulatory issues. Thus, there is a strong need for methods that generate properly equipped DC which efficiently induce immune responses and in particular provide improved clinical responses.

In addition, ex vivo generated DC could also be implemented as therapeutic vaccine in treatment of some chronic infectious diseases such as HIV and hepatitis B and C, where traditional vaccine approach is not working efficiently. The results of the preclinical and first clinical[4-5] studies indicate that DC-based immunotherapy could be a promising strategy for treatment of patients with chronic infections by HIV-1 and hepatitis B and C. As with cancer immunotherapy, efficient clinical response against these intracellular infectious agents is associated with induction of Th1 helper response required for development of CD8+ effector cells[5]. Therefore, one can expect that ex vivo generated dendritic cells should have the same characteristics both for treating cancer and chronic infectious diseases.

DISCLOSURE OF THE INVENTION

In a first aspect the present invention relates to a method for generating dendritic cells by employing temperatures below 37° C. during the development of progenitor cells and immature dendritic cells.

In a second aspect the invention relates to a population of dendritic cells, wherein said cells are generated by the method for generating dendritic cells by employing temperatures below 37° C. during the development of progenitor cells and immature dendritic cells.

In a third aspect the invention relates to a pharmaceutical composition comprising a population of dendritic cells wherein said cells are generated by the method for generating dendritic cells by employing temperatures below 37° C. during the development of progenitor cells and immature dendritic cells.

In a fourth aspect the invention relates to use of the population of cells, wherein said cells are generated by the method for generating dendritic cells by employing temperatures below 37° C. during the development of progenitor cells and immature dendritic cells, for the stimulation and/or expansion of T cells In a fifth aspect the invention relates to use of the population of cells, wherein said cells are generated by the method for generating dendritic cells by employing temperatures below 37° C. during the development of progenitor cells and immature dendritic cells, for inducing an immune response in a subject.

In a sixth aspect the invention relates to use of the population of cells, wherein said cells are generated by the method for generating dendritic cells by employing temperatures below 37° C. during the development of progenitor cells and immature dendritic cells, for the manufacture of a medicament for the treatment or prevention of cancer or infectious diseases.

BRIEF DESCRIPTION OF THE DRAWING(S)

The file of this patent contains at least one drawing executed in color. Copies of this patent with color drawings will be provided by the Patent and Trademark Office upon request and payment of the necessary fee.

The invention is explained in detail below with reference to the drawings, in which.

DETAILED DESCRIPTION OF THE INVENTION

The present invention is described in detail below. For the purpose of interpretation the following definitions shall apply and whenever appropriate, terms used in the singular shall also include the plural and vice versa.

Definitions

"Differentiation step" as used herein, means the step wherein the cells are allowed to differentiate in response to defined differentiation factors.

"Maturation step" as used herein, means the step wherein the cells are allowed to mature in response to the presence of maturation factors.

"Decreased temperature" or "Lowered temperature" as used herein, means that the temperature is below 37° C.

A method for generating dendritic cells is the well known method of J. H. Peters who was the first to describe the ability of monocytes to transform into DC-like cells in vitro, first spontaneously and later in the presence of GM-CSF and IL-4[6]. After publications by Romani et al., (1994)[7] and Sallusto & Lanzavecchia (1994)[8] monocytes cultured in the presence of these two cytokines became widely used for preparation of DC. The procedure starts with isolation of monocytes from peripheral blood and their culture in the presence of GM-CSF and IL-4 for 5-7 days. The obtained cells have properties of immature DC characterized by low levels of co-stimulatory molecules and high endocytic activity. During maturation induced by LPS, TNF-alpha or other maturation agents the cells significantly up-regulate co-stimulatory and accessory molecules, such as e.g. CD40, CD80, CD83 and CD86, and down-regulate endocytic activity.

In vitro tissue culture is in general performed at 37° C. It is known that Langerhans cells are functionally active at the ambient temperature of the skin at 29-31° C., and a few studies have documented the biological effect in vitro of lowered culture temperatures in cell systems such as e.g. Chinese Hamster Ovary (CHO) cells and swine alveolar macrophages.

In contrast to work by Basu et al. (2003) investigating the effect of fever-like temperatures on DC activation and maturation, decreased temperatures has only in few cases been tested for their effect on mammalian cell growth. Dexter et al. (1977) suggested using 33° C. for culturing haematopoietic stem cells[9]. Athanasas-Platsis et al. (1995) found that expression of the langerhans cell marker, CD1a on monocytes was up-regulated during a 24 hours culturing at 34° C. as compared to 37° C.[10].

No one has to our knowledge disclosed how to generate immature or mature dendritic cells by employing decreased temperatures.

In one embodiment the invention relates to a method for generating dendritic cells by employing temperatures below 37° C. during the development of progenitor cells and immature dendritic cells.

IL-10 is a negative regulator of DC development and is produced during activation of a monocyte cell line in the presence of GM-CSF[11]. Kirkley et al. (2003) reported that IL-10 production by a macrophage cell line stimulated with LPS was significantly reduced in response to a decrease in incubation temperature from 37° C. to 31° C.[12]. The reduced temperature comprised in the method of the present invention may thus provide improved conditions for DC generation by means of e.g. low IL-10 concentration.

The effect of culturing monocytes in the presence of GM-CSF and IL-4 at different temperatures (31° C., 34° C. and 37° C.) on the level of expression of CD1a of immature DC, a molecule extremely sensitive to the inhibitory effect of IL-10 has been tested. We found that DC generated at lower temperatures had higher levels of its expression. All further experiments were performed at 34° C. The next principle observation was that IL-10 levels detected in the supernatants of the cultures were indeed significantly lower upon culture at lower temperature.

In one embodiment the invention relates to a method, wherein the generated dendritic cells are mature dendritic cells.

In one embodiment the invention relates to a method, wherein the development of progenitor cells and immature dendritic cells comprises differentiation of said cells.

In one embodiment the invention relates to a method, wherein the temperature is below 37° C. during differentiation.

In one embodiment the invention relates to a method, wherein the temperature is 31° C. to 37° C. The temperature may be any of the temperatures 31° C., 32° C., 33° C., 34° C., 35° C., or 36° C.

In one embodiment the invention relates to a method, wherein the temperature is 34° C.

In one embodiment the invention relates to a method, wherein the progenitor cells are autologous progenitor cells.

In one embodiment the invention relates to a method, wherein the progenitor cells are selected from myeloid progenitor cells or stem cells.

In one embodiment the invention relates to a method, wherein the myeloid progenitor cells are monocytes.

In another embodiment the invention relates to a population of dendritic cells are generated by the method according to the invention.

In one embodiment the invention relates to a population of dendritic cells, wherein said cells express CCR7 and/or IL-12p70.

In one embodiment the invention relates to a population of dendritic, wherein said cells express CD1a, $CD14^{low}$, CD83, CD86 and $IL-10^{low}$.

In one embodiment the invention relates to a population of dendritic cells, further comprising at least one antigen presented in associated with a MHC molecule at the cell surface.

In one embodiment the invention relates to a population of dendritic cells, wherein said at least one antigen is a tumor antigen.

In one embodiment the invention relates to a population of dendritic cells, wherein said tumor antigen is selected from a group comprising; Cancer/testis antigen, lineage specific differentiation antigen, tumor over-expressed antigen, mutated or aberrantly expressed antigen, and viral antigen.

In a further embodiment the invention relates to the use of the population of dendritic cells as defined above, for the stimulation and/or expansion of T cells.

In one embodiment the invention relates to the use of the population of dendritic cells for the stimulation or expansion of T cells, wherein said T cells are autologous T cells.

In one embodiment the invention relates to the use of the population of dendritic cells for the stimulation or expansion of T cells, wherein said use is an in vitro use.

In yet a further embodiment the invention relates to the use of the population of dendritic cells for inducing an immune response in a subject.

In yet another embodiment the invention relates to a pharmaceutical composition comprising a population of dendritic cells wherein said population is as defined above.

In one embodiment the invention relates to a use of the pharmaceutical composition as a medicament.

In one embodiment the invention relates to a pharmaceutical composition comprising a population of dendritic cells further comprising conventional adjuvants and excipients.

In an alternative embodiment the invention relates to the use of the dendritic cells for the manufacture of a medicament for the treatment or prevention of cancer or infectious diseases.

In one embodiment the invention relates to the use of the population of dendritic cells for the manufacture of a medicament for the treatment or prevention of cancer or infectious diseases, wherein said cancer is selected from the group comprising: melanoma, breast cancer, colon cancer and lung cancer, or could be any kind of cancer.

In one embodiment the invention relates to the use of the population of dendritic cells for the manufacture of a medicament for the treatment or prevention of cancer or infectious diseases, wherein the infectious diseases is selected from the group comprising: HIV and hepatitis or other chronic infectious diseases.

EXAMPLES

This invention is now illustrated by the following examples that are not intended to be limiting in any way.

Example 1: Generation of the Dendritic Cells Employing Decreased Temperature

Dendritic cells were typically generated from buffy-coat obtained from the blood bank. 60 mL of buffy-coat was diluted with 60 mL of Ca-free and Mg-free Dulbecco's Phospate Buffered Saline (DPBS, Product No. BE17-512F, Cambrex, Belgium), and applied to four 50-mL tubes each containing 15 mL Lymphoprep (Product No. 1053980, AXIS-SHIELD PoC AS, Norway). After centrifugation (460 g, 30 min, 20° C.), 10-20 mL of the upper plasma layer were transferred to separate tubes. It was estimated that this is approximately 40% plasma (diluted plasma). Final preparation of plasma includes addition of heparin (25 IU/mL) and centrifugation (1500 g, 15 min, 4° C.). Mononuclear cells were harvested from the interface, diluted twice with EDTA-containing DPBS and washed by 4-5 centrifugations, the first at 250 g, the second at 200 g and the following at 150 g, all centrifugation at 4° C., 12 min, Before the last centrifugation cells were counting using Coulter Counter (Beckman Coulter, model Z2), and amount of monocytes was estimated as number of cells with an average size of about 9□m). The cells may be stored at −80° C. (in diluted plasma with 10% DMSO, $10^7$ monocytes per vial), or used immediately in experiments.

The cells were resuspended in adsorption medium (RPMI 1640 (Cambrex) supplemented with 2 mM L-glutamine and 2% plasma) at a concentration of $2\times10^6$ monocytes/mL. 5 mL of the cell suspension was placed in T25 non-TC-treated Falcon flasks. After 1 hour of adsorption at 37° C., non-adherent cells were removed, adherent cells were rinsed twice with warm RPMI 1640, and 7 mL cultivation medium (RPMI 1640 supplemented with 2 mM L-glutamine and 1% plasma) were added to each flask.

The flasks were placed at different temperatures: 31° C., 34° C. and 37° C. in separate $CO_2$-incubators. Differentiation factors GM-CSF and IL-4 at final concentrations of 100 ng/mL and 50 ng/mL respectively were added at day 1, 3 and 5.

TNF-alpha at a final concentration of 10 ng/mL was added at day 6 to induce maturation and the temperature was raised to 37° C. for the last 24 hr of incubation.

At day 7, the cells were harvested and their phenotype was determined by FACS analysis. Cells were stained using the direct conjugated antibodies CD1a-phycoerythrin (PE), CD14-fluorescein isothiocyanate (FITC), CD83-PE, CD86-PE, HLA-DR, -P, -Q-FITC (all from Pharmingen, Beckton Dickinson, Brøndby, Denmark) and CCR7-FITC(R&D Systems Europe, Abington, UK). Appropriate isotype controls were used. Samples were analyzed using FACSCalibur Flow Cytometer (Beckton Dickinson) and CELLQuest software (Beckton Dickinson).

Figure 1:
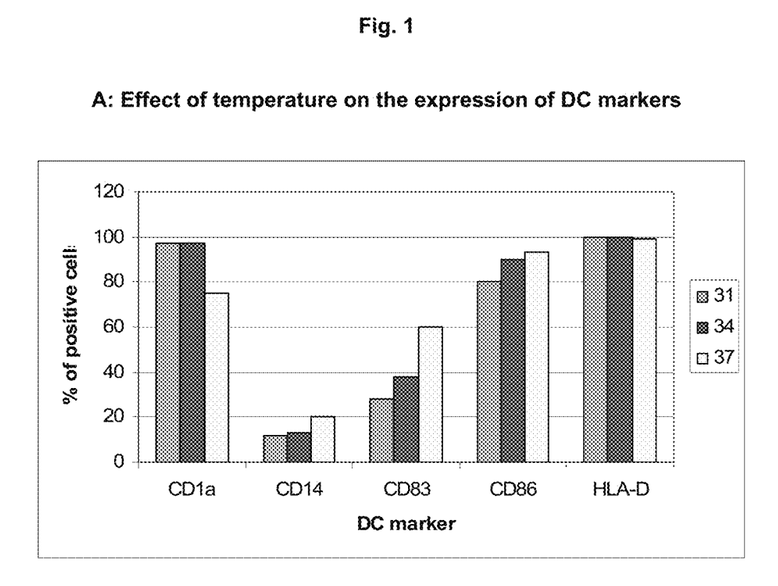
FIG. 1 illustrates the effect of temperature on important co-stimulatory and accessory surface molecules of DC.

The result of representative experiments is shown in FIG. 1. More cells cultured at reduced temperatures express CD1a as compared to cells cultured at 37° C., whereas less CD83 and CD86 positive cells were observed for cell populations cultured at lower temperatures. Mean fluorescence index (MFI) for CD1a was twice as high upon culture at 31° C. and 34° C. in comparison with 37° C. The degree of maturation as judged by the percentage of CD83 and CD86 expressing DC was lower at 31-34° C. This reflects either a lower sensitivity to maturation factors of cells cultured at reduced temperature, or that the maturation process itself requires a temperature of 37° C.

Example 2: The Effect of Decreased Temperature on the Production of IL-10

Figure 2:
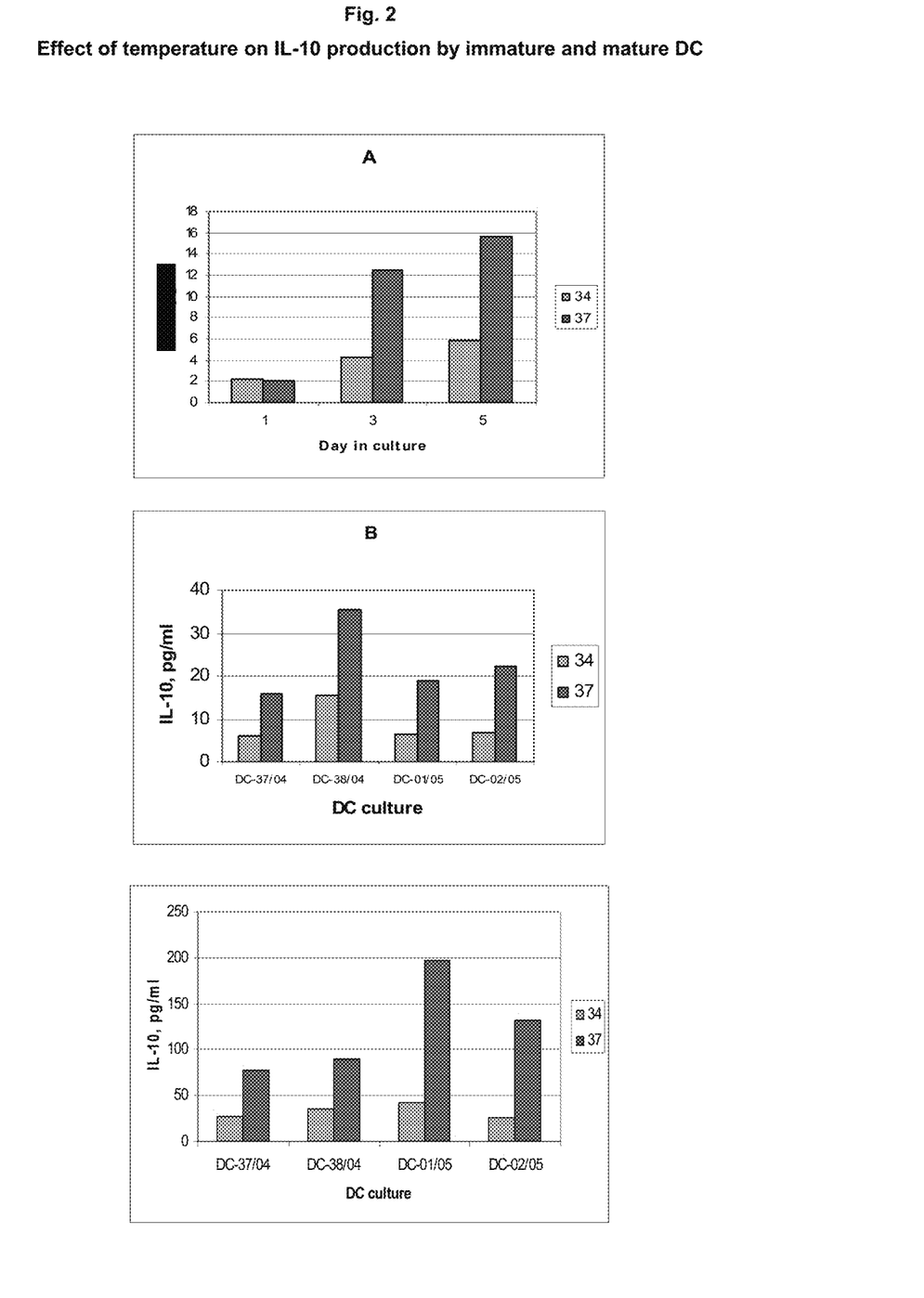
FIG. 2 illustrates the effect of temperature on the amount of IL-10 produced by DC during the initial days of culture (A) and produced by immature DC (B) and mature DC (C).

The production of IL-10, which is a negative regulator of DC, was investigated during differentiation of monocytes into dendritic cells. Its concentration in culture supernatant taken at days 1, 3 and 5 was measured. Production of IL-10 was measured by sandwich ELISA that included capture antibody (Ab), standard or sample, biotinylated detection Ab, and HRP-streptavidin using "Ready-Set-Go" kit from eBioscience essentially according to the manufacturers' recommendations with some modifications. After overnight binding of capture Ab to the Nunc maxisorp 96-well plates and washing, the blocking step was extended to at least 3 hrs at RT. A standard curve was generated by seven serial dilutions of the standard, starting with 200 pg/mL of IL-10. Standards and samples were incubated at RT for 2 hrs followed by incubation at 4° C. overnight. The next steps were performed according to the manufacturers' protocol. Tetramethylbenzidine substrate solution from the same kit was used in enzymatic reaction of HRP, and after terminating the reaction, optical density was measured with wavelength correction as difference between readings at 490 and 620 nm. The results of one of such experiments are presented in FIG. 2A. Spontaneous production of IL-10 by monocytes was low during the first day, and was significantly up-regulated after addition of GM-CSF and IL-4 at day 1. Cells cultured at 34° C. until day 5 produce in general significantly lower amounts of IL-10 compared to cells cultured at 37° C. Test of several DC cultures at day 5 showed a similar pattern (FIG. 2B). The reduced production of IL-10 at 34° C. as compared to 37° C. continued even after washing the cells at day 5, placing them at 37° C., adding maturation agent at day 6 and collecting supernatants at day 8 (FIG. 2C). These results indicate that cells cultured at temperatures below 37° C. acquire a stable phenotype of low IL-10 production.

Example 3: The Effect of Decreased Temperature on the Production of IL-12p70

We have also investigated effect of temperature on production of IL-12p70. Production of IL-12p70 was measured by sandwich ELISA that included capture Ab, standard or sample, biotinylated detection Ab, and HRP-streptavidin. Kits "DuoSet ELISA development System" for IL-12p70 (R&D Systems) were used essentially according to the manufacturers' recommendations with some modifications. After overnight binding of capture Ab to the Nunc maxisorp 96-well plates and washing, the blocking step was extended to at least 3 hrs at RT. Standard curve was generated by seven serial dilutions of the standard, starting 500 pg/mL of IL-12p70. Standards and samples were incubated at RT for 2 hrs followed by incubation at 4° C. overnight. The next steps were performed according to the manufacturers' protocol. Hydrogen peroxide-tetramethylbenzidine mixture was used as a substrate solution for HRP, and after terminating the enzymatic reaction optical density was measured with wavelength correction as difference between readings at 490 and 620 nm.

TABLE 1

Effect of temperature during the first 5 days of culture on the production of IL-12p70 during maturation induced by MCM mimic.

| DC culture | Temperature of incubation until day 5 | Production of IL-12p70 during maturation, pg/ml |
| --- | --- | --- |
| 36/04-3-3 | 34° C. | 35.1 |
| 36/04-3-4 | 37° C. | 14.1 |
| 17/05-2-1 | 34° C. | 55.2 |
| 17/05-2-3 | 37° C. | 35.7 |
| 18/05-2-1 | 34° C. | 19.0 |
| 18/05-2-3 | 37° C. | 3.7 |

As can be seen (Table 1), cells generated at 34° C. produce significantly higher levels of IL-12p70.

Example 4: Selection of Tissue Culture Plastic

We have compared two types of tissue culture plastics: Non-tissue culture polystyrene (PS) (Product No. 353813, T25 BD-Bioscience, USA) and Primaria™ plastic (Product No. 353813, T25 BD-Bioscience, USA). The experiment were set up similar to the procedure described in example 1, using plastic surfaces pre-treated for 15-45 min. with 2% of autologous plasma as a source for components such as e.g. extra cellular components like fibrinogen and fibronectin, in serum free AIM-V media at 34° C. until day 5, after which the cultures were placed at 37° C. The maturation agents; TNF alpha, IL-1 beta, IL-6 and prostaglandin E2 were added at day 6, and the cultures were harvested at day 8.

Progenitor cells have depending on growth condition the option to develop into macrophages or DC. After a few days in culture cells destined for developing into macrophages will form adherent cell cultures whereas cells destined for developing into DC will form more loosely attached cell cultures. Initially an equal number of cells were seeded and adhered to the different tissue culture plastic. Inspection of DC cultures from day 6 by light microscopy revealed a significantly less number of adherent cells on Primaria™ plastic in comparison with cells grown on another type of plastic. In general, cultures grown on Primaria™ plastic also appeared more "clean" i.e. less debris, reflecting less extent of the cell death during maturation.

We tested the use of different concentration of plasma for pre-treatment of plastic. No significant differences in the properties of DC were observed upon treatment of Primaria™ plastic with 2%, 10%, 20% or 40% plasma (data not shown). However, we noticed that the amount of contaminating lymphocytes decreased with increasing plasma concentration up to 10%. Therefore we included the step of treating Primaria™ plastic with 10% plasma in the method described in experiment 1 in the subsequent experiments.

In the following experiments we have compared the method of the invention to a "standard method" which is performed as described below unless otherwise indicated.

Dendritic cells were typically generated from buffy-coat obtained from the blood bank. 60 mL of buffy-coat was diluted with 60 mL of Ca-free and Mg-free Dulbecco's Phosphate Buffered Saline (DPBS, Product No. BE17-512F, Cambrex, Belgium), and applied to four 50-mL tubes, each containing 15 mL Lymphoprep (Product No. 1053980, AXIS-SHIELD PoC AS, Norway). After centrifugation (460 g, 30 min, 20° C.), 10-20 mL of the upper plasma layer were transferred to separate tubes. Mononuclear cells were harvested from the interface, diluted twice with PBS EDTA without calcium and magnesium and washed by 3 centrifugations, the first at 250 g, the second at 175 g and the last at 110 g, all centrifugation at 4° C., 12 min. Before the last centrifugation cells were counted using a Coulter Counter (Beckman Coulter, model Z2), and the amount of monocytes was estimated as number of cells with an average size of about 9 µm).

The cells were resuspended in adsorption medium (RPMI 1640 (Cambrex) supplemented with 2 mM L-glutamine and 1% heat inactivated autologous plasma) at a concentration of $2 \times 10^6$ monocytes/mL. 5 mL of the cell suspension was placed in T25 non-treated Primaria™ flasks. After 1 hour of adsorption at 37° C., non-adherent cells were removed, and 5 mL cultivation medium (RPMI 1640 supplemented with 2 mM L-glutamine and 1% plasma) were added to each flask.

At day 1 the media was changed with fresh media. At day 3 2 ml media were added. At day 5 all non-adherent cells were harvested and placed in T25 Primaria™ flasks with fresh media.

The flasks were placed at 37° C. in $CO_2$-incubator. Differentiation factors GM-CSF and IL-4 at final concentrations of 100 ng/mL and 50 ng/mL respectively were added at day 1, 3 and 5.

TNF-α or Cytokine cocktail (IL-1, IL-6, TNF-α and PGE-2) was added at day 6 to induce maturation.

At day 7, the cells were harvested and their phenotype was determined by FACS analysis.

Example 5: IL-12p70 Production

Figure 3:
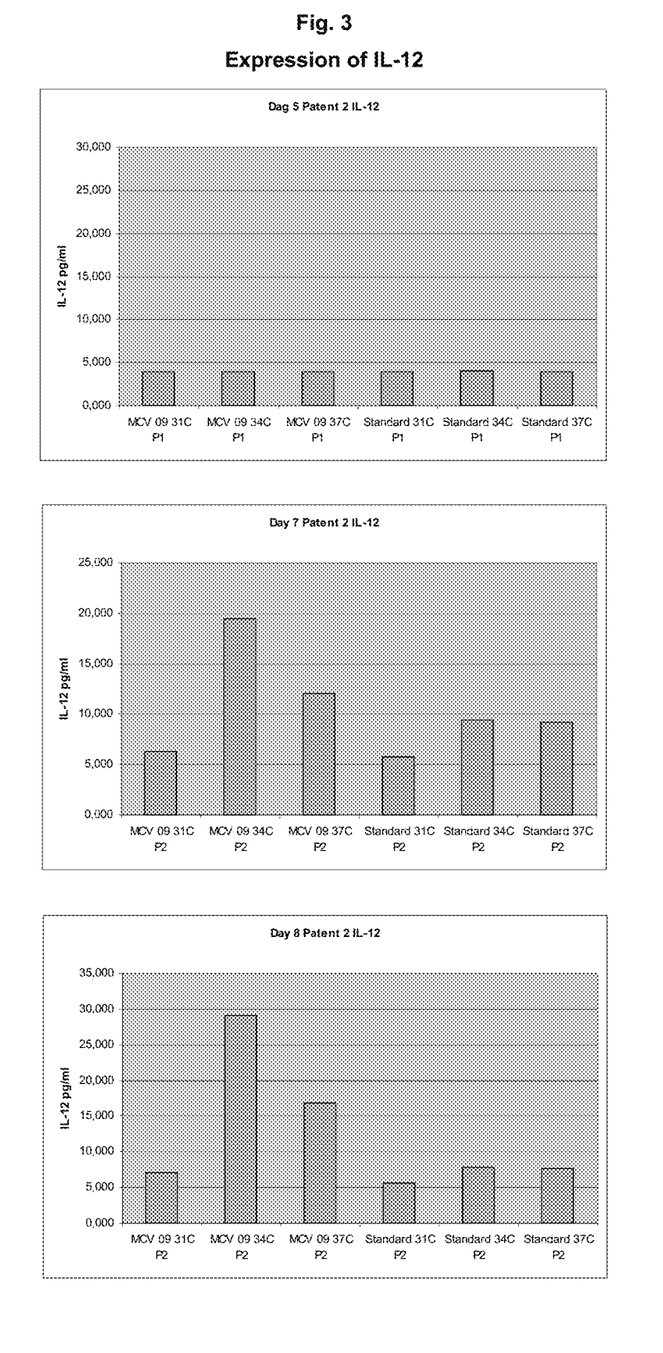
FIG. 3 illustrates the effect of the temperatures 31° C., 34° C. and 37° C. on the IL-12p70 production by immature (A) and mature (B, C) dendritic cells generated by the new method and a standard method.

FIG. 3 illustrates the measuring of IL-12 p70 production over two days (day 7 and 8) we were able to shown that the dendritic cells generated by the new method produce significantly higher amounts of IL-12 p70 than dendritic cells generated by a standard method.

Example 6: Expression of CCR7

Figure 4:
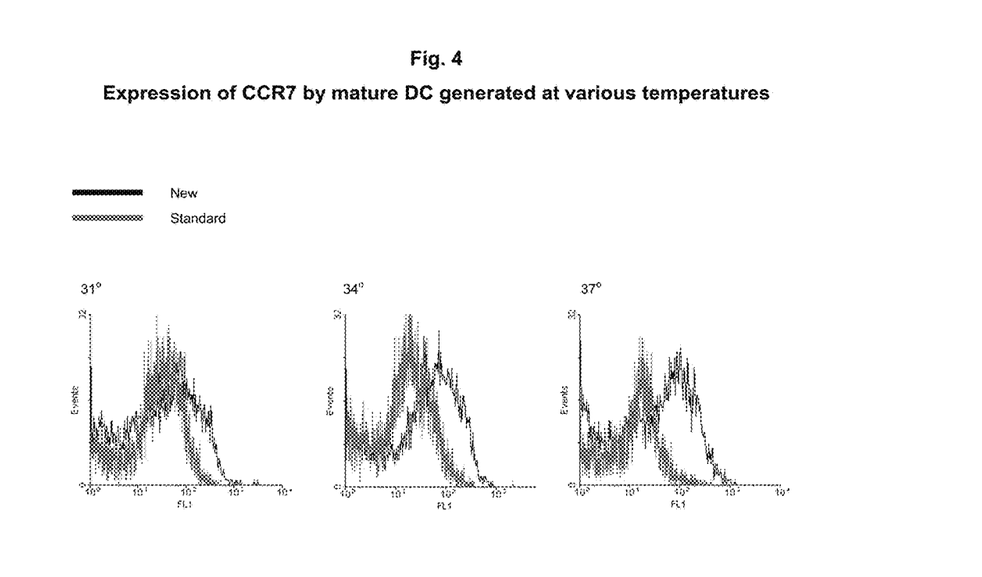
FIG. 4 illustrates the effect of low temperature on CCR7 expression.

To investigate effect of low temperature on CCR7 expression, we employed maturation cocktail consisting of IL-1 beta, IL-6, TNF-alpha and prostaglandin E2 instead of using only TNF-alpha. The result of the experiments presented in FIG. 4 is comparing three different temperatures with the new method and a standard method. It can be seen that the expression of CCR7 is higher with the new method as compared to the standard method.

We also tested the functionality of the CCR7 receptor expression by dendritic cell generated by the new method in a standard migration assay (Chemotx Disposable Chemotaxis System (Model 116-5) from Neuro Probe, Gaithersburg, Md., USA). Here we saw dendritic cell migration towards the chemokines CCL19 with DC generated by the new method (data not shown) verifying expression of a functional CCR7 receptor.

Example 7: Cell Yield

The new method describe herein also showed increased cell yield compared to standard method. In three different runs we found a higher cell yield at all temperatures tested (31° C., 34° C. and 37° C.) with the new method compared to standard method See table 2.

TABLE 2

| Method | Temperature | | |
|---|---|---|---|
| | 31° C. | 34° C. | 37° C. |
| New method | | | |
| 1) | $2.2 \times 10^6$ | $2.0 \times 10^6$ | $2.6 \times 10^6$ |
| 2) | $2.6 \times 10^6$ | $1.8 \times 10^6$ | $1.3 \times 10^6$ |
| 3) | $1.7 \times 10^6$ | $2.0 \times 10^6$ | $1.6 \times 10^6$ |
| Standard method | | | |
| 1) | $1.7 \times 10^6$ | $1.1 \times 10^6$ | $0.9 \times 10^6$ |
| 2) | $1.3 \times 10^6$ | $1.6 \times 10^6$ | $0.6 \times 10^6$ |
| 3) | $0.8 \times 10^6$ | $1.0 \times 10^6$ | $0.6 \times 10^6$ |

Example 8: Batch-to-Batch Marker Variations of DC Generated by the New Method In compliance with GMP requirements for the production of dendritic cells for medical purposes, there should be low batch to batch variations in properties of dendritic cells. For this purpose we performed preparation of dendritic cells from the blood of 8 different donors during period of three weeks, using the same lots of all employed reagents and 0.5% of autologous plasma as addition to AIM-V medium. For the comparison, production of DC using "standard" method (37° C.) was performed. The experiments were performed on thawed PBMC. Table 3 summarizes the properties of DC generated in these experiments. In contrast to the high variability in properties of DC generated by the "standard" method, very low degree of variability in properties of DC obtained by the new method was observed.

TABLE 3

Different markers expressed in percentage of dendritic cells generated by either a standard method or the new method.

| Donor | CD1a | | CD14 | | $CD86_{high}$ | | HLA-D | | CD83 | | CCR7 | |
|---|---|---|---|---|---|---|---|---|---|---|---|---|
| | S | N | S | N | S | N | S | N | S | N | S | N |
| 23/05 | 56 | 44 | 73 | 18 | 28 | 70 | 98 | 100 | 28 | 70 | ND | ND |
| 24/05 | 41 | 85 | 2 | 1 | 49 | 99 | 99 | 100 | 75 | 99 | ND | ND |
| 25/05 | 0 | 10 | 17 | 1 | 80 | 99 | 99 | 100 | 83 | 99 | 63 | 98 |
| 26/05 | 50 | 69 | 9 | 1 | 90 | 99 | 100 | 100 | 91 | 99 | 85 | 98 |
| 27/05 | 53 | 86 | 9 | 1 | 93 | 100 | 100 | 100 | 93 | 100 | 90 | 99 |
| 28/05 | 69 | 73 | 37 | 12 | 25 | 86 | 97 | 100 | 41 | 86 | 18 | 81 |
| 29/05 | 66 | 84 | 60 | 2 | 43 | 96 | 98 | 100 | 43 | 99 | 17 | 95 |

TABLE 3-continued

Different markers expressed in percentage of dendritic cells
generated by either a standard method or the new method.

| | CD1a | | CD14 | | CD86$_{high}$ | | HLA-D | | CD83 | | CCR7 | |
|---|---|---|---|---|---|---|---|---|---|---|---|---|
| Donor | S | N | S | N | S | N | S | N | S | N | S | N |
| 30/05 | 86 | 89 | 25 | 1 | 63 | 99 | 100 | 100 | 63 | 99 | 56 | 98 |
| X: | 53 | 68 | 29 | 5 | 59 | 94 | 99 | 100 | 65 | 94 | 55 | 95 |

S: standard method,
N: method according to the invention,
ND: Not determined,
X: Mean value.

Figure 5A:
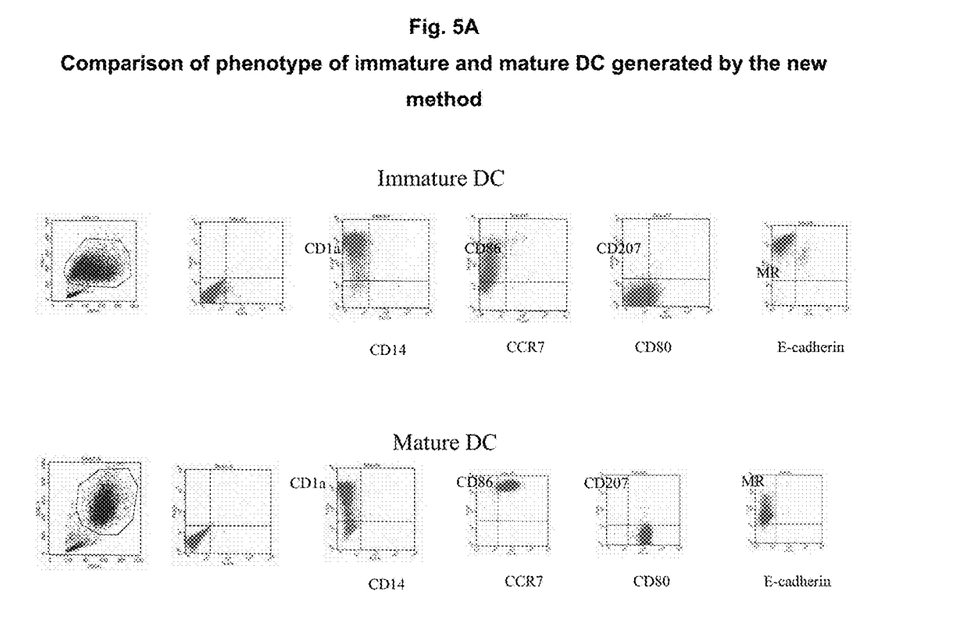
FIG. 5 illustrates the phenotype of immature and mature DC generated by method according to the invention (A) and in comparison with a "standard" method (B).

Finally, FIG. 5A represents phenotypes of immature (day 5) and mature (day 8) dendritic cells generated by the new method. Here we also measured expression of CD80, mannose receptor (MR) and two markers of Langerhans cells—CD207 (langerin) and E-cadherin. As could be seen, the cells generated by the method according to the invention are not Langerhans cells.

Figure 5B:
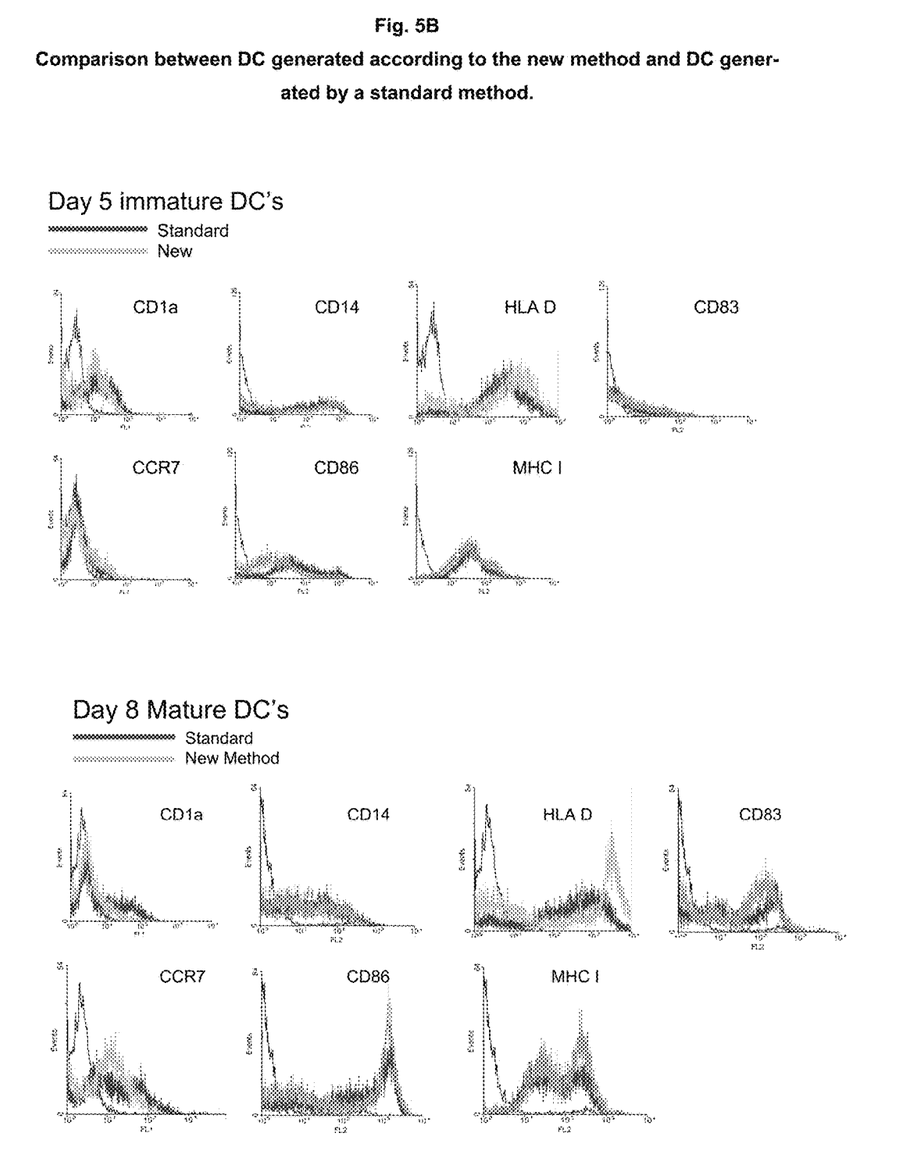

FIG. 5B represents the phenotype of immature (day 5) and mature (day 8) dendritic cells generated by the new method and a standard method. Here we have stained the cells for the expression of standard DC markers. The immature cells (day 5) show a more clean CD1a population. The mature population (day 8) is showing a high and uniform HLA D, CD83 and CD86 expression in cells generated by the new method as compared to the standard method. Also CCR7 expression is more uniformly expressed with the new method.

Example 9: Stability of Dendritic Cells Generated by the New Method

Figure 6:
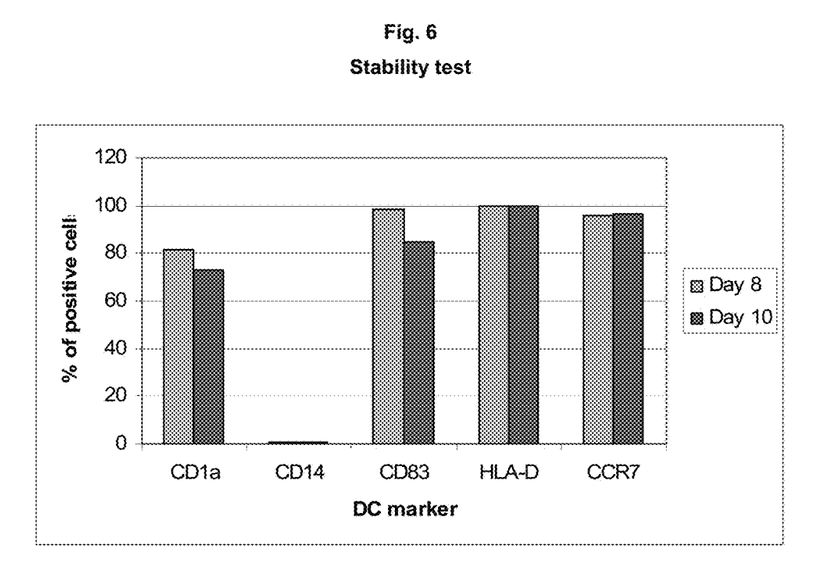
FIG. 6 illustrates the phenotypic stability of mature DC over time.

After injection into the organism dendritic cells should migrate and arrive at the lymph node in order to stimulate T cells. It is therefore very important that DC maintain their phenotype for several days. A common way of performing stability-test is to harvest the cells at day 8, wash out of the cytokines and continue culturing the cells in the absence of stimulatory cytokines. We have performed this kind of experiments by culturing cells without cytokines for two days. FIG. 6 represent the results of the FACS analysis of DC harvested at day 8 and after additional two days of culture. It appears clearly that the expression of measured parameters: CD1a, CD14, CD83, HLA-D and CCR7 remain largely unchanged and thus the phenotype remains stable.

Figure 7:
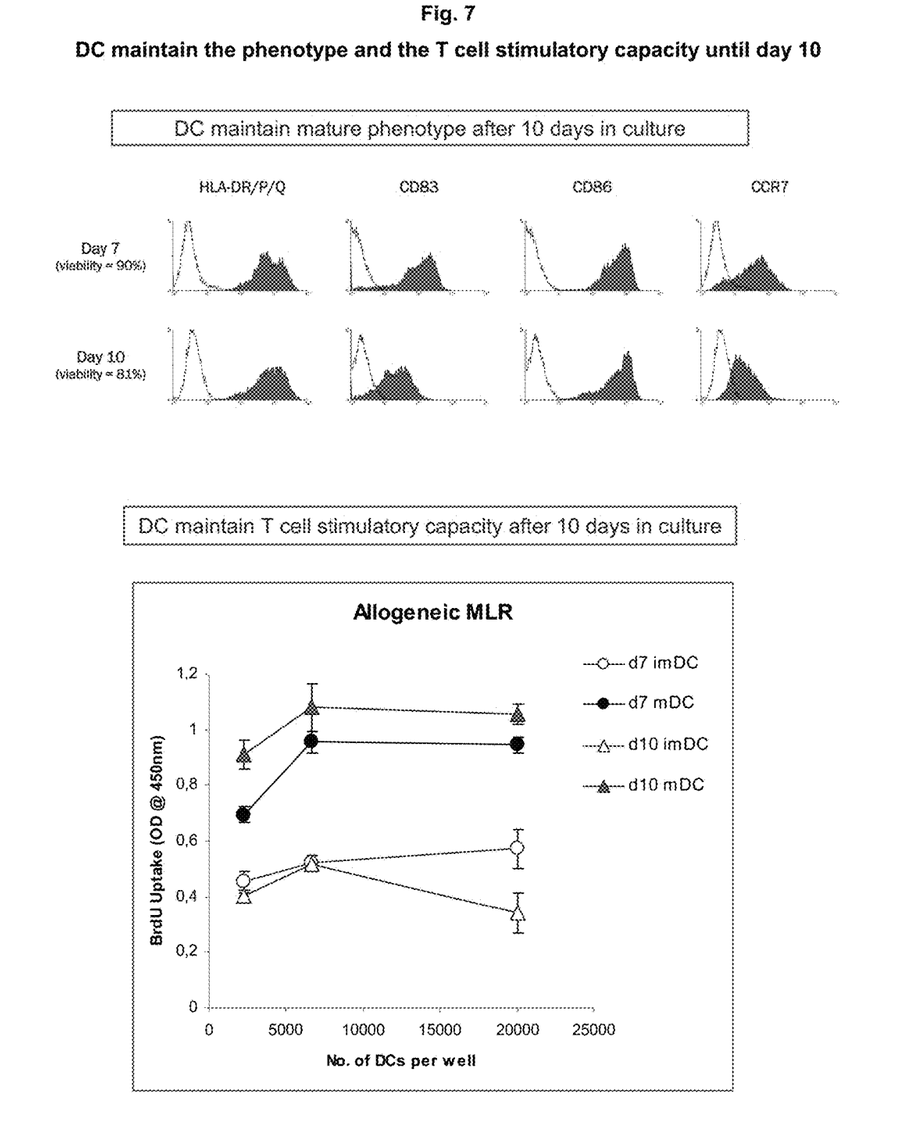
FIG. 7 illustrates the phenotype and allo-stimulatory (MLR) activity of DC at day 7 and day 10.

In a similar experiment, without washing out cytokines at day 8, we tested the both the phenotype and the allo-stimulatory activity of dendritic cells at day 7 or day 10. FIGS. 7A and 7B shows the phenotype and the allo-stimulatory activity respectively. The results shows that the allo-stimulatory effect is still high after 10 days of culture and the phenotypic profile at day 10 resembles the profile measured day 7 verifying high stability of generated dendritic cells.

Example 10: Allo-Stimulation by Dendritic Cells Generated by the New Method

Figure 8:
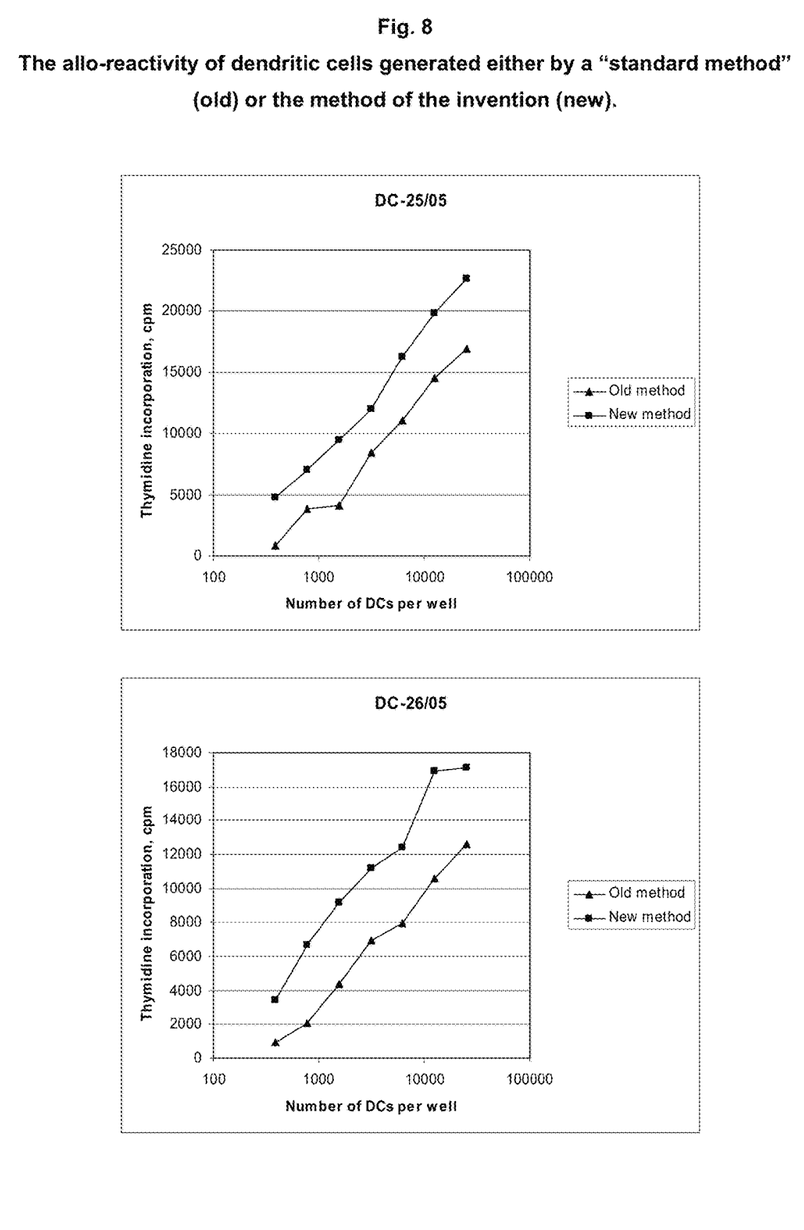
FIG. 8 illustrates the allo-stimulatory activity of DC generated with the method according to the invention and a "standard" method.

We have compared the allo-stimulatory abilities of DC obtained by the "standard" method and the method according to the invention. Cells were cultured in RPMI 1640 medium with 5% AB human serum. Responder cells were mononuclear cells obtained from healthy donors by density separation of peripheral blood buffy-coat. Stimulator cells were irradiated mature dendritic cells obtained after a 2 days exposure to the maturation cytokine cocktail as described in the example 4. Stimulator cells, 0.1×10$^6$ cells in 100 µl, were mixed with titrated numbers of stimulator cells (in 100 µl) as shown in FIG. 8 and cultured for 5 days in U-bottom 96-well microtiter plates. $^3$H-thymidine (0.1 µCurie/mL) was added for the last 18 hrs. Subsequently, the cells were harvested for scintillation counting. Data are given as the mean cpm values of four replicate cultures. The Wilcoxon test was used to estimate differences between the two methods used for the generation of DC. As could be seen, dendritic cells obtained by the method according to the invention have 3-10 times higher allo-stimulatory activity.

Figure 9:
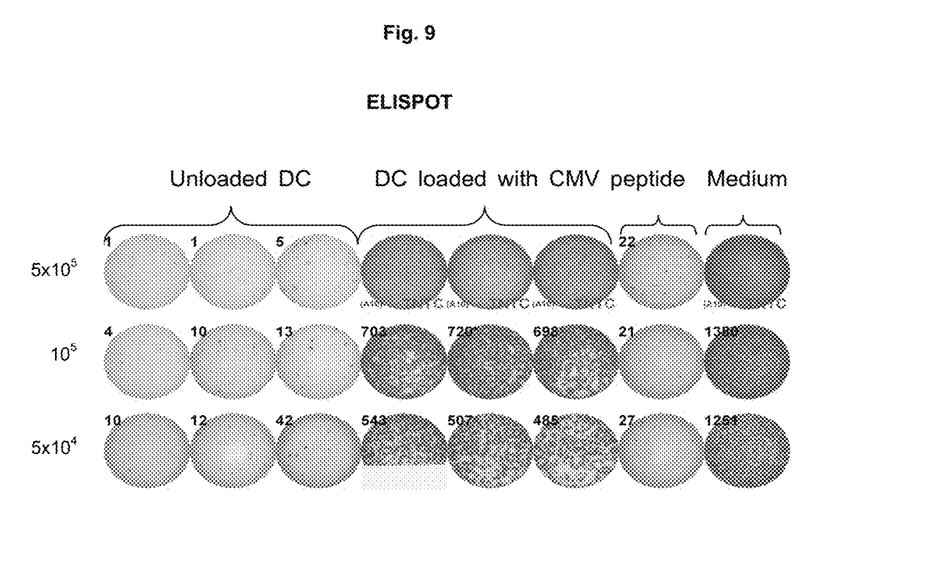
FIG. 9 illustrates functional presentation of CMV-antigen measured by induction of IFN-γ (ELISPOT assay).

Example 11: Antigen Presentation by the Dendritic Cells Generated by the New Method To elucidate the potential of DC to present antigen to T cells, an INFγ ELISPOT assay was conducted with T cells stimulated by DC naked or pulsed with a CMV peptide. The INFγ ELISPOT assay was chosen as the assay provides a clear result on a single cell level and that T cells upon encounter with antigen presented by APC release INFγ. The CMV peptide used is restricted to HLA-A2 and the donor material was known to be HLA-A2 positive, and as 80% of the population has a CMV response this virus model was chosen. FIG. 9 depicts the results of an ELISPOT assay showing that there is a strong response from the T cells stimulated with DC loaded with the CMV peptide indicating that these DC are capable of antigen presentation to T cells.

REFERENCES

1. Heufler, C., Koch, F., Stanzl, U., Topar, G., Wysocka, M., Trinchieri, G., Enk, A., Steinman, R. M., Romani, N., and Schuler, G. Interleukin-12 is produced by dendritic cells and mediates T helper 1 development as well as interferon-gamma production by T helper 1 cells. Eur. J. Immunol., 26: 659-668, 1996.
2. Scandella, E., Men, Y., Gillessen, S., Forster, R., and Groettrup, M. Prostaglandin E2 is a key factor for CCR7 surface expression and migration of monocyte-derived dendritic cells. Blood, 100: 1354-1361, 2002.
3. Jonuleit, H., Kuhn, U., Muller, G., Steinbrink, K., Paragnik, L., Schmitt, E., Knop, J., and Enk, A. H. Proinflammatory cytokines and prostaglandins induce maturation of potent immunostimulatory dendritic cells under fetal calf serum-free conditions. Eur. J. Immunol., 27: 3135-3142, 1997.
4. Chen, M., Li, Y. G., Zhang, D. Z., Wang, Z. Y., Zeng, W. Q., Shi, X. F., Guo, Y., Guo, S. H., and Ren, H. Therapeutic effect of autologous dendritic cell vaccine on patients with chronic hepatitis B: a clinical study. World J. Gastroenterol., 11: 1806-1808, 2005.
5. Lu, W., Arraes, L. C., Ferreira, W. T., and Andrieu, J. M. Therapeutic dendritic-cell vaccine for chronic HIV-1 infection. Nat. Med., 10: 1359-1365, 2004.
6. Peters, J. H., Xu, H., Ruppert, J., Ostermeier, D., Friedrichs, D., and Gieseler, R. K. Signals required for differentiating dendritic cells from human monocytes in vitro. Adv. Exp. Med. Biol., 329: 275-280, 1993:
7. Romani, N., Gruner, S., Brang, D., Kämpgen, E., Lenz, A., Trockenbacher, B., Konwalinka, G., Fritsch, P. O., Steinman, R. M., and Schuler, G. Proliferating dendritic cell progenitors in human blood. J. Exp. Med., 180: 83-93, 1994.
8. Sallusto, F. and Lanzavecchia, A. Efficient presentation of soluble antigen by cultured human dendritic cells is maintained by granulocyte/macrophage colony-stimulating factor plus interleukin 4 and downregulated by tumor necrosis factor a. J. Exp. Med., 179:1109-1118, 1994.
9. Dexter, T. M., Allen, T. D., and Lajtha, L. G. Conditions controlling the proliferation of haemopoietic stem cells in vitro. J. Cell Physiol, 91: 335-344, 1977.
10. Athanasas-Platsis, S., Savage, N. W., Winning, T. A., and Walsh, L. J. Induction of the CD1a Langerhans cell marker on human monocytes. Arch. Oral Biol., 40:157-160, 1995.
11. Lehmann, M. H. Recombinant human granulocyte-macrophage colony-stimulating factor triggers interleukin-10 expression in the monocytic cell line U937. Mol. Immunol., 35: 479-485, 1998.
12. Kirkley, J. E., Thompson, B. J., and Coon, J. S. Temperature alters lipopolysaccharide-induced cytokine secretion by RAW 264.7 cells. Scand. J. Immunol., 58: 51-58, 2003.

The invention claimed is:

1. A method of generating mature dendritic cells having a stable phenotype characterized by expression of CCR7 by a mean value of 95% of the cell population and a stable IL-10$^{low}$ phenotype, the method comprising:
   culturing monocytes at a temperature selected from 31° C., 32° C., 33° C., and 34° C.,
   differentiating the monocytes into immature dendritic cells by addition of GM-CSF and IL-4 during the first 5 days of culturing whilst maintaining a temperature selected from 31° C., 32° C., 33° C., and 34° C., and
   on day 6 performing a maturation step for 1 to 3 days by incubating the immature dendritic cells at 37° C. in monocyte conditioned medium mimic (MCM mimic), wherein during maturation an IL-12p70 concentration of at least 19 pg per ml MCM mimic is achieved.

2. The method according to claim 1, wherein the monocytes are autologous cells.

3. The method according to claim 1, wherein the monocytes are differentiated from stem cells.

4. The method according to claim 1, wherein the GM-CSF is added to achieve a concentration of 100 ng per mL medium and the IL-4 is added to achieve a concentration of 50 ng per mL medium.

5. The method according to claim 1, wherein the GM-CSF and the IL-4 are added during day 1 of the culturing of monocytes.

6. The method according to claim 1, wherein the GM-CSF and the IL-4 are added during days 1, 3 and 5 of the culturing of monocytes.

* * * * *

UNITED STATES PATENT AND TRADEMARK OFFICE
CERTIFICATE OF CORRECTION

PATENT NO. : 9,771,558 B2  
APPLICATION NO. : 12/086050  
DATED : September 26, 2017  
INVENTOR(S) : Alexei Kirkin et al.

Page 1 of 1

It is certified that error appears in the above-identified patent and that said Letters Patent is hereby corrected as shown below:

On the Title Page

Item (73), change Assignee from "DANDRIT DIOTECH A/S" to "DANDRIT"

Signed and Sealed this  
Fourteenth Day of May, 2019

Andrei Iancu  
*Director of the United States Patent and Trademark Office*